US012758772B2

(12) United States Patent
Kulah et al.

(10) Patent No.: US 12,758,772 B2
(45) Date of Patent: Oct. 13, 2026

(54) MEMS-BASED COCHLEAR IMPLANT

(71) Applicant: Haluk Kulah, Ankara (TR)

(72) Inventors: Haluk Kulah, Ankara (TR); Hasan Ulusan, Ankara (TR); Aykan Batu, Ankara (TR); Ozge Zorlu, Ankara (TR); Salar Chamanian, Ankara (TR); Ebru Ozgur, Ankara (TR)

(73) Assignee: Haluk Kulah, Ankara (TR)

( * ) Notice: Subject to any disclaimer, the term of this patent is extended or adjusted under 35 U.S.C. 154(b) by 489 days.

(21) Appl. No.: 18/258,223

(22) PCT Filed: Dec. 17, 2020

(86) PCT No.: PCT/TR2020/051317
§ 371 (c)(1),
(2) Date: Jun. 19, 2023

(87) PCT Pub. No.: WO2022/132064
PCT Pub. Date: Jun. 23, 2022

(65) Prior Publication Data

US 2024/0050745 A1 Feb. 15, 2024

(51) Int. Cl.

| | |
|---|---|
| ***A61N 1/36*** | (2006.01) |
| ***A61N 1/378*** | (2006.01) |
| ***H02N 2/18*** | (2006.01) |
| ***H04R 17/00*** | (2006.01) |
| ***H04R 25/00*** | (2006.01) |
| ***H10N 30/30*** | (2023.01) |

(52) U.S. Cl.
CPC ....... *A61N 1/36038* (2017.08); *A61N 1/3785* (2013.01); *A61N 1/3787* (2013.01); *H02N 2/181* (2013.01); *H02N 2/188* (2013.01); *H04R 17/00* (2013.01); *H04R 25/606* (2013.01); *H10N 30/306* (2023.02)

(58) Field of Classification Search
CPC .. A61N 1/3785; A61N 1/36038; H02N 2/188; H10N 30/306
See application file for complete search history.

(56) References Cited

U.S. PATENT DOCUMENTS 3,456,134 A * 7/1969 Ko ........................ A61N 1/3785 331/116 R
3,712,962 A 1/1973 Epley
5,856,722 A * 1/1999 Haronian ................. H03H 9/50 310/309
6,261,224 B1 * 7/2001 Adams ...................... H04R 1/46 607/57

(Continued)

FOREIGN PATENT DOCUMENTS

WO WO-2013081560 A1 * 6/2013 ........... A61N 1/3785

OTHER PUBLICATIONS

Robert Fettiplace, et al., The sensory and motor roles of auditory hair cells, Nature Reviews Neuroscience, 2006, pp. 19-29, vol. 7.

(Continued)

*Primary Examiner* — Eric D. Bertram
(74) *Attorney, Agent, or Firm* — Bayramoglu Law Offices LLC

(57) ABSTRACT

A fully implantable device for mimicking the natural hearing mechanism of the ear and producing auditory signals to stimulate the auditory nerves is provided.

20 Claims, 8 Drawing Sheets

(56) References Cited

U.S. PATENT DOCUMENTS

| | | | | |
|---|---|---|---|---|
| 6,264,603 | B1 * | 7/2001 | Kennedy | H04R 25/558 607/55 |
| 8,634,924 | B1 * | 1/2014 | Ko | H04R 25/606 607/136 |
| 9,630,007 | B2 * | 4/2017 | Kulah | A61N 1/36038 |
| 10,022,541 | B2 | 7/2018 | Pfeifer | |
| 2003/0012390 | A1 * | 1/2003 | Franks | A61N 1/36036 381/114 |
| 2005/0113633 | A1 * | 5/2005 | Blau | H04R 25/606 607/57 |
| 2005/0245990 | A1 * | 11/2005 | Roberson | A61N 1/36036 607/57 |
| 2007/0026043 | A1 * | 2/2007 | Guan | C09D 153/00 525/437 |
| 2007/0191863 | A1 * | 8/2007 | De Juan | A61B 34/70 606/108 |
| 2009/0018559 | A1 * | 1/2009 | Buevich | A61L 31/148 606/151 |
| 2010/0168808 | A1 * | 7/2010 | Citron | A61L 31/16 623/8 |
| 2010/0295419 | A1 * | 11/2010 | Fujii | H02N 2/188 29/25.35 |
| 2014/0303688 | A1 * | 10/2014 | Kulah | H04R 25/606 607/57 |
| 2016/0184596 | A1 * | 6/2016 | Fried | A61N 1/0539 607/45 |
| 2017/0084815 | A1 * | 3/2017 | Choo | H02N 2/188 |

OTHER PUBLICATIONS

Levent Beker, et al., Stimulating auditory nerve with Mems harvesters for fully implantable and self-powered cochlear implants, Transducers 2013, pp. 1663-1666.

Salar Chamanian, et al., An Adaptable Interface Circuit With Multistage Energy Extraction for Low-Power Piezoelectric Energy Harvesting MEMS, IEEE Transactions on Power Electronics, 2019, pp. 2739-2747, vol. 34 No. 3.

* cited by examiner

MEMS-BASED COCHLEAR IMPLANT

CROSS REFERENCE TO RELATED APPLICATIONS

This application is the national phase entry of International Application No. PCT/TR2020/051317, filed on Dec. 17, 2020, the entire contents of which are incorporated herein by reference.

TECHNICAL FIELD

The invention relates to MEMS-Based Cochlear Implant which is on a fully implantable device for mimicking the natural hearing mechanism of the ear and producing auditory signals to stimulate the auditory nerves.

BACKGROUND

Human peripheral auditory system (FIG. 1) is composed of outer ear (pinna), middle ear (ear canal, tympanic membrane (1), ossicles), and inner ear (cochlea). The range of human hearing varies from 20 Hz up to 20 kHz acoustic waves. Pinna and auditory canal (FIG. 1) amplify the incoming sound waves according to the incoming acoustic wave frequency. Tympanic membrane (1) is connected to the ossicles (the malleus, incus, and stapes) in the middle ear which also add further amplification to the sound vibration and transfer these vibrations to the oval window (3) of the cochlea (4). The movement of the stapes stimulates the inner ear leading to an electrochemical activity associated with the cochlear hair cells found on the basilar membrane that stimulates the auditory nerves. An example is given in R. Fettiplace, C. M. Hackney, "The sensory and motor roles of auditory hair cells" Nat. Rev. Neurosci., vol. 7, no. 1, pp. 19-29, 2006.

Sensorineural hearing impairment is caused from irreversible damage to cochlear hair cells rendering them non-functional/missing. Cochlear implants (CIs) are used to bypass the damaged hair cells and directly stimulate the auditory nerve by means of a cochlear electrode, thus opening a way for the treatment of sensorineural hearing loss. In a typical cochlear implant system, external and internal components form a complete working system/device. External components comprise a microphone, a sound processor, a battery and a wireless emitter.

Internal components comprise a receiver and the cochlear electrode. The microphone collects the acoustic information in the environment and the captured acoustic waves are processed and transmitted to the cochlear electrode via a receiver implanted at the rear head behind the ear.

These devices suffer from daily/frequent battery recharge/replacement requirement, damage risk of external components, and aesthetic concerns combined with psychological effects on the patients. The exposure of the external components to the outer world can lead to a damage easily due to impact and water. On the other hand, hearing impairment is a disease affecting the patient's quality of life by limiting the social interaction of him/her with the environment. For young patients this situation may also have adverse effects on the psychological health.

The major drawback of conventional CIs is that, they replace the entire natural hearing mechanism with electronic hearing, even though most parts of the middle ear are operational. Besides, the power-hungry units such as RF transceiver and processors cause limitations in continuous operation due to battery capacity.

Up to now, various devices have been recorded to substitute the microphone component of cochlear implants to reduce the battery need of them.

US 2003/0012390 A1 describes a resonator bars as a vibration detector with distinct resonance frequency resonator corresponding to their thickness with piezoelectric. This device used in conventional cochlear implants, however it doesn't provide a solution for energy consumption concerns.

An implantable piezoelectric hearing aid was reported in U.S. Pat. No. 3,712,962 A, where a single piezoelectric transducer is placed on middle ear between bones to sense incoming sound and generate signals to stimulate the auditory system. The generated signal is not large enough for direct stimulation of electrodes without electronics. On the other hand, the electronics and powering of such electronics was not specified.

The same concern applies to US. Pub. No. 20050113633 using single elliptic thin piezoelectric element to convert ossicles vibration to electrical signal. Previous argument: single elliptic thin element produces low signal voltage that is not enough to stimulate the auditory nerve without electronics.

U.S. Pat. No. 10,022,541 B2 disclosed a low power electronic device for cochlear implant. The system including sensing, processing, and stimulation circuits is utilized to interface single piezoelectric transducer and stimulate electrodes in cochlea. The need of a battery is inevitable and providing different power supplies is problematic, while powering up the system is matter of serious concern.

Micro-fabricated piezoelectric transducers are widely used to convert mechanical vibrations to electrical domain and they offer solutions for cochlear implants (CIs) as a sound sensor and also power source due to its small size and relatively high energy density. Utilizing this capability, micro piezoelectric transducers can be used for (i) exploiting the functional parts of the middle ear and mimicking the hair cells in the cochlea (4) via electrodes and (ii) harvesting energy from vibrations in the hearing system. An example of micro-fabricated piezoelectric transducers being used to conert mechanical vibrations to electrical domain is given in L. Beker, Ö. Zorlu, N. Göksu, and H. Külah, "Stimulating auditory nerve with MEMS harvesters for fully implantable and self-powered cochlear implants," in 2013 Transducers Eurosensors XXVII: The 17th International Conference on Solid-State Sensors, Actuators and Microsystems (TRANSDUCERS EUROSENSORS XXVII), 2013, pp. 1663-1666.

If MEMS-based multi-frequency transducers are used for sensing and mechanical filtering of the acoustic signals, (U.S. Pat. No. 9,630,007 (as in point 1 above)), external microphone, transceiver and electronic filtering circuitry—all of which necessitate external components and result in a power-hungry operation—can be eliminated. Therefore, this can lead to elimination of bulky external components and significant reduction of power demand which can be supplied via MEMS based energy harvesting transducer.

This invention is an improvement over the patent of H. Külah, et al., "Energy harvesting cochlear implant" U.S. patent application Ser. No. 14/355,213, filed Dec. 2, 2011, now U.S. Pat. No. 9,630,007. In that patent, the fundamental of the fully implantable cochlear implant is introduced.

SUMMARY

The present invention is related to a MEMS-Based Cochlear Implant system that meets the requirements mentioned above, eliminates all of the disadvantages and brings about some new advantages.

Research studies conducted over those Fundamentals (mentioned in Prior Art About The Invention) since then, advanced to a significantly improved concept for the FICI. These improvements necessitates filing of a new patent for this significantly improved concept, which are briefly; (i) separate transducers for energy harvesting and sound sensing, (ii) sound processing and stimulation by ultra-low power interface circuit instead of direct stimulation by transducer, (iii) wireless recharging, (iv) vacuum packaging of transducers, (v) recharging through a standard earplug via a simple tone generator application running on a smart phone.

This invention introduces a fully implantable cochlear implant system (FICI) composed of the multi-frequency acoustic transducer and an energy harvesting system using piezoelectric effect. All components of the FICI system are implemented in middle and inner ear. The stack of acoustic transducer and energy harvester are mounted on one of the ossicles on the ossicular chain (2) or the tympanic membrane (1) to sense incoming sound and extract acoustic energy, respectively. Electronics are necessary to interface acoustic sensor and energy harvester in order to generate the required impulse for the stimulation of the relevant auditory nerves via implanted electrode in cochlea (4) and recharge the battery. Transducers are fabricated and packaged using Micro-Electro-Mechanical Systems (MEMS) fabrication techniques and implanted into middle ear, all coated with a biocompatible material. A wireless data transfer unit is also included for patient fitting and system diagnosis. The invention promises high quality electronic hearing aid by help of mimicking the natural hearing mechanism and eventually eliminates components of a conventional cochlear implant outside the body and batteries to be frequently replaced.

The system includes transducer and energy harvester making use of piezoelectricity to generate signal of acoustic waves and extract incoming energy which is to be implanted to middle ear on tympanic membrane or ossicles. The device utilizes interface electronic to sense and process signals for electrically stimulating the relevant auditory nerves corresponding to selected frequency of sound. Implanted rechargeable battery provides required power where energy harvesting system including piezoelectric harvester and interface circuit recharge the battery and provide regulated supply voltage. The device further compromises RF coils and related electronics for patient fitting and diagnosis as well as power transfer to the battery as a support for energy harvesting system. The RF coil and an interface circuit are implanted under the skin beside the rechargeable battery. The invention in complete mimics the natural operation of an auditory system, therefore eliminates the use of microphone, sound processor, and transmitter that are currently used externally in conventional cochlear implants.

BRIEF DESCRIPTION OF THE DRAWINGS

The figures used to better explain a MEMS-Based Cochlear Implant developed with this invention and their descriptions are as follows.

DETAILED DESCRIPTION OF THE INVENTION

The parts in the FIGS. have each been numbered and the references of each number has been listed below.

1 Tympanic membrane
2 Ossicular Chain
3 Oval Window
4 Cochlea
5 Round Window
20 Piezoelectric piece
21 Cantilever Beam
22 Tip Mass
33 Base To better explain MEMS-Based Cochlear Implant developed with this invention, the details are as presented below.

Figure 1:
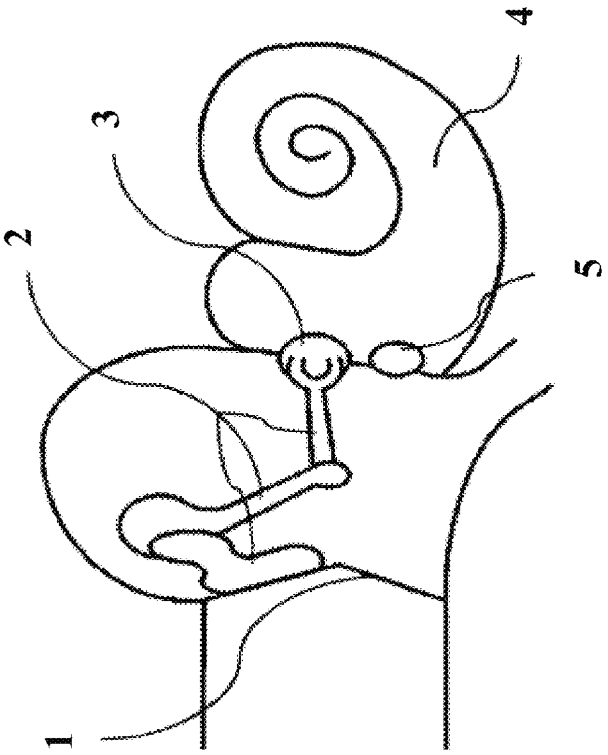
FIG. 1 (Prior Art)
FIG. 1 is a schematic view of the human ear.

With reference to FIG. 1, the present invention describes a self-powered fully implantable device to electrically stimulate the auditory nerves found in the cochlea (4) using a cochlear electrode for recovering the impaired hearing. Piezoelectric effect is used to convert mechanical vibrations to electrical domain for both sound sensing and energy harvesting purposes. The sound transducer according to this invention is implanted to middle ear on tympanic membrane or on ossicle chain (2) to sense the frequency of the vibrations of the incoming Sound pressure waves according to its mechanical frequency selective structure. This invention utilizes ultra-low power interface electronics to amplify and process generated signals over transducer. The calibrated amplitude of the signals is transferred to the electrodes according to cochlear frequency map for stimulating auditory nerves. MEMS fabricated piezoelectric harvester is stacked with sound transducer to generate required power from vibrations of middle ear organelles (2). In this invention, an autonomous interface electronic manages the extracted energy and provides regulated supplies for stimulation electronics. The architecture of interface electronics contains passive and active circuits with two storage elements including a capacitor and a rechargeable battery. Passive energy extraction circuit can charge up the storage element with no initial energy in either reservoirs. The circuit manage charge flow to storage elements and control activation of other electronics through start-up circuits to achieve autonomous operation. A rechargeable battery and the interface electronics associated with a coil are implanted under the skin. This coil is used as a wireless transfer for patient fitting and recharging the battery via attachable external coil as a back-up/support for the energy harvesting system.

Figure 2:
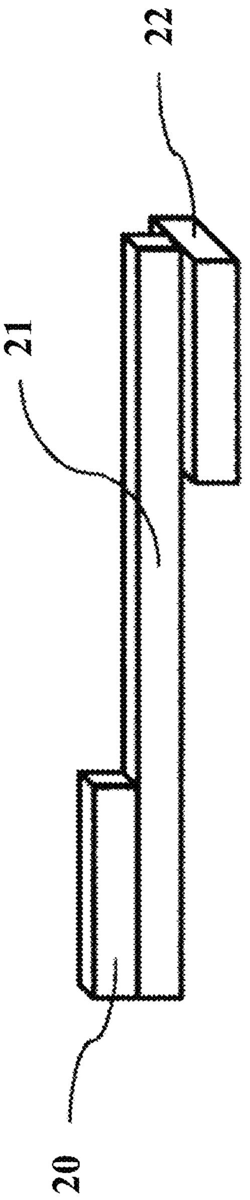
FIG. 2 depicts a beam of transducer or energy harvester according to the invention in detail.

Information about Major Components:

Energy Harvesting:

One of the most important features of the FICI is its novel battery charging methodology by which the device harvests energy through the vibration generated as a result of sound waves fed by a simple earplug connected to a tone generator. This can be a simple application running on a smartphone or a similar mobile device, or through ambient sound. Battery recharging is realized through a harvesting transducer based on MEMS piezoelectric cantilever FIG. 2, and a power conditioning interface circuit, which extracts energy from the transducer and manage extracted energy to charge storage element for powering up sound processing and stimulator IC. The autonomous power unit offers an important improvement in the long-term use of the implants with ultra-low power (250 μW-500 μW range power consumption) and efficient electronics. The harvesting transducer is optionally vacuum packaged, and high quality-factor cantilever die operating at acoustic bands with preferably specific resonance frequencies, not interfering with the frequency bands of acoustic sensor.

A piezoelectric energy harvester is to be placed to a location that the vibrations due to sound waves can be detected; either in the middle ear cavity connected to one or more hearing elements such as umbo, ossicles or ear drum; or under the skin tissue of ear canal. The goal is to have high acoustic energy (40-90 dB SPL) and utilize ear canal amplification effect. The eardrum (Tympanic membrane (1)) vibrates with the sound waves coming through the ear channel (auditory canal). Pinna and auditory canal amplifies the incoming sound waves according to the incoming wave frequency. The piezoelectric harvester design and mounting point have minimum damping effect of on hearing elements and perceive maximum incoming energy by designing at ear canal amplification frequency.

Power conditioning IC is an autonomous self-adaptive system to extract acoustic energy via piezoelectric energy harvester for supplying power to neural stimulation electronics. Integrated circuit provides practical MEMS piezoelectric harvesting system and is compact enough to be implantable in the limited area within middle ear or its close periphery. The IC boosts and manages extracted power and provides regulated power supply to sub-units of the system. An example of a power conditioning IC is given in S. Chamanian, H. Uluşan, A. Koyuncuoğlu, A. Muhtaroğlu and H. Külah, "An Adaptable Interface Circuit With Multistage Energy Extraction for Low-Power Piezoelectric Energy Harvesting MEMS," IEEE Transactions on Power Electronics, vol. 34, no. 3, pp. 2739-2747, March 2019. doi: 10.1109/TPEL.2018.2841510.

Energy harvesting unit is for fulfilling the power demand of this ultra-low power cochlear implant. However, as an implanted device cannot be replaced frequently, a back-up solution is integrated to the FICI device for power supply. In addition to energy harvester, a wireless power transfer unit is included in the package for recharging the battery, whenever the performance of energy harvester cannot cover the consumption of FICI package. Refer to "Wireless power and data transmission" section for this back-up recharging unit.

Sound Sensing and Stimulation:

The FICI uses frequency selective piezoelectric cantilevers, in a similar way to the cochlear hair cells, to generate the signals for neural stimulation. This eliminates most of the power-hungry electronics, such as microphones, RF transceiver, and active band pass filters, while utilizing the healthy portions of the middle ear. By this way, the FICI operates at low power, as it does not require continuous RF transmission and microphone. Also, the piezoelectric cantilevers with band-pass characteristics simplify the electronics.

Acoustic Sensor:

FICI's sound detection unit: acoustic sensor/transducer is an array of piezoelectric cantilevers (FIG. 3) placed on the eardrum or ossicles. The Piezoelectric cantilevers convert acoustic vibration into electrical signal required for neural stimulation at specified frequency channels.

Figure 4:
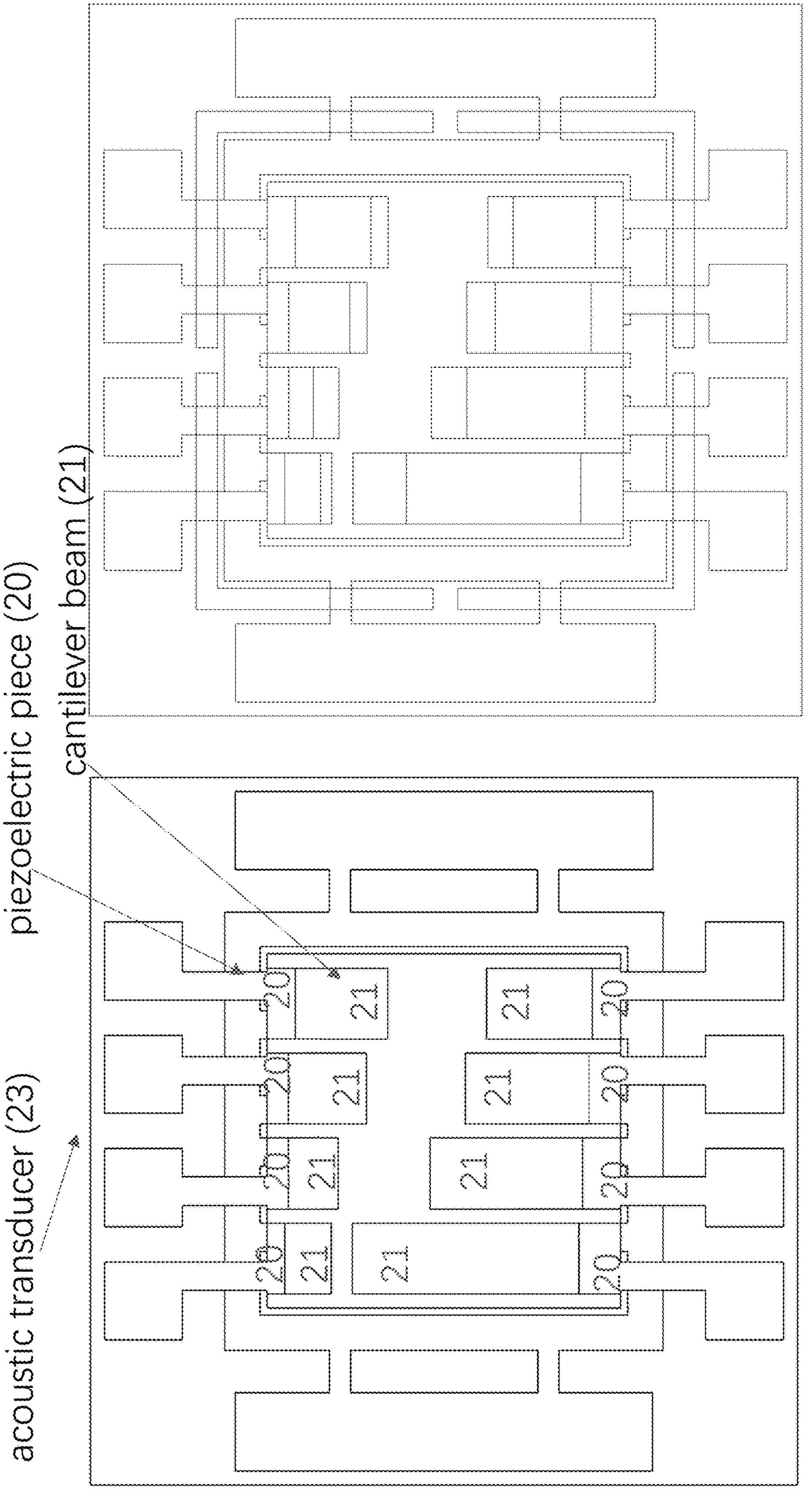
FIG. 4 depicts another possible transducer according to the invention.

This invention proposes a feasible solution to the challenges such as volume and mass limitations, frequency range, and power requirements. The transducer based on mechanical sensors is compacted since all sensing devices (multi-frequency piezoelectric transducers) can be gathered either on a single layer (FIG. 4) or stacked layers (FIG. 5) for covering specific frequency range of human hearing band. Micro cantilevers are spaced linearly and logarithmically according to the distribution of daily sound waves in hearing band. They provide mechanical filtering and mimic the natural operation of the cochlea, which is a major innovation of this invention.

Sound Processing and Stimulation Interface Circuit:

Low-powered signal conditioning interface circuit is required to accomplish the FICI system. In this invention, fully integrated interface circuit, with substantially reduced power dissipation (<500 μW) compared to conventional CIs (10 mW-40 mW), processes signals from the piezoelectric cantilevers with different frequencies and stimulates the auditory neurons inside cochlea (4) consistently according to the power level and frequency of the acoustic input signal.

The sensor outputs are amplified, range-compressed into AC current waveforms and rectified. The envelopes of the rectified signals are extracted and are selectively sampled as a reference for the stimulation current generator equipped with patient fitting function. Adjusted biphasic stimulation current is delivered to the auditory neurons while protecting them from excess charge damage.

Figure 6:
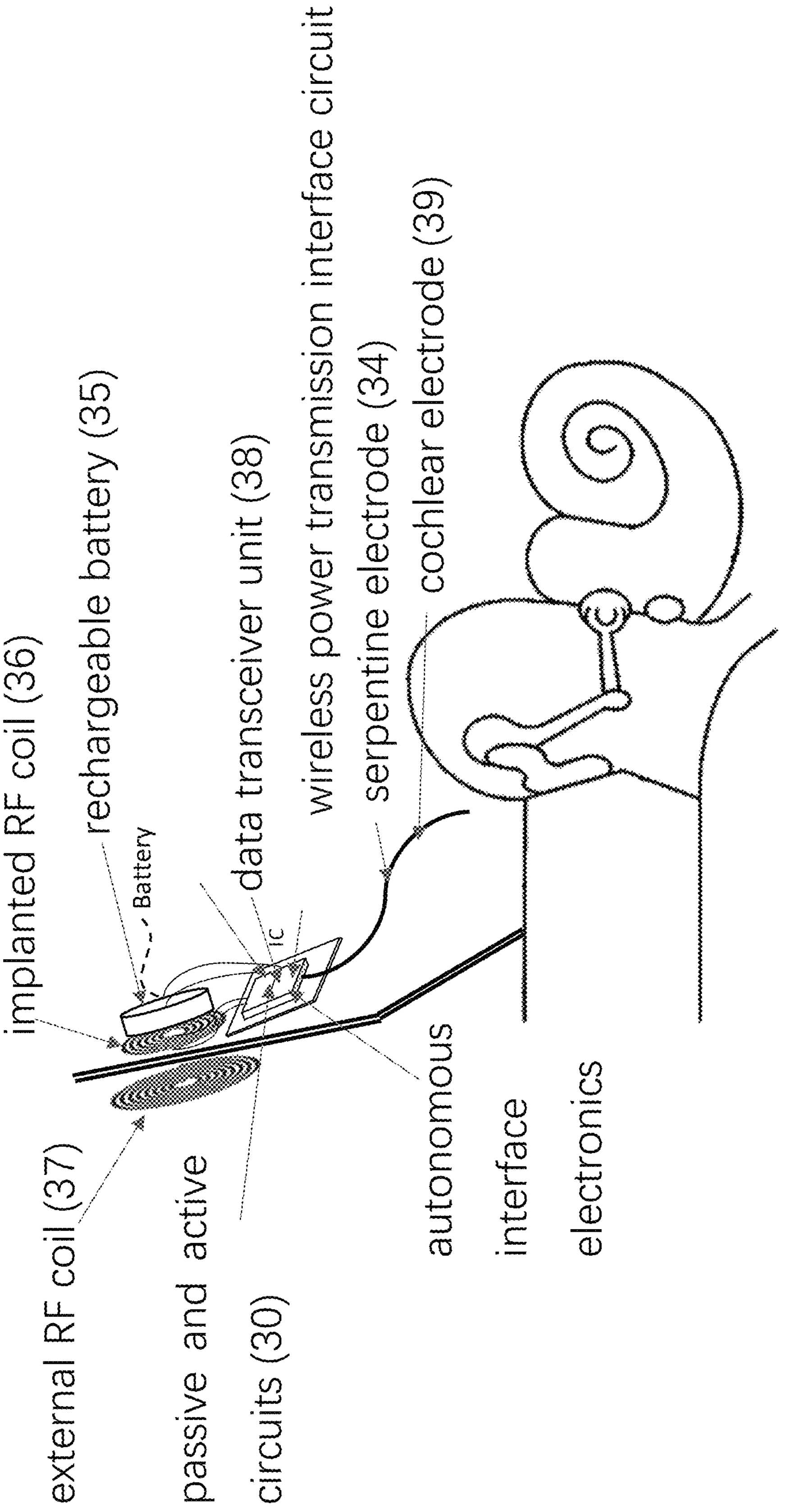
FIG. 6 depicts a schematic of installed RF coil and battery associated with Interface circuits according to the invention.

Wireless Power and Data Transmission:

The battery implanted under the skin is recharged by an acoustic energy harvesting system. In order to have a back-up and a supporting source to the energy harvester, wireless power transmission interface circuit is included. An RF coil placed next to the battery under the skin (FIG. 6) and external RF coil aligned to the implanted one is utilized not only to charge the battery when harvested energy is not sufficient but also for data transfer for patient fitting and diagnosis. It should be clearly stated that this charging system is different from the conventional cochlear implant power transfer unit, which requires continuous RF power transmission to operate, while in this charging unit introduced for the FICI, RF wireless transmission will be activated just for short duration as complementary source to charge the battery.

The charging operation is done with inductively coupled RF coils. The efficiency of the transmission, and effect of misalignment between transmitter and receiver units during charging is minimized with specific measures without using any magnets. These coils facilitate high power transfer in range of 1 mW up to 50 mW and high-speed data transmission 4 Mb/s as well as low area occupation.

Data Transmission:

Any implanted device is required to be calibrated initially, and in the long term; monitored and recalibrated. For this purpose, a reliable data transmission unit is vital. Then, FICI includes a data transceiver unit with the following functions:

i. Receiving data from outside to inside for patient fitting,
ii. Back telemetry in order to validate the received data via transferring data from inside to outside. This is realized with same inductively coupled RF coils or other data transfer channels.

Figure 5:
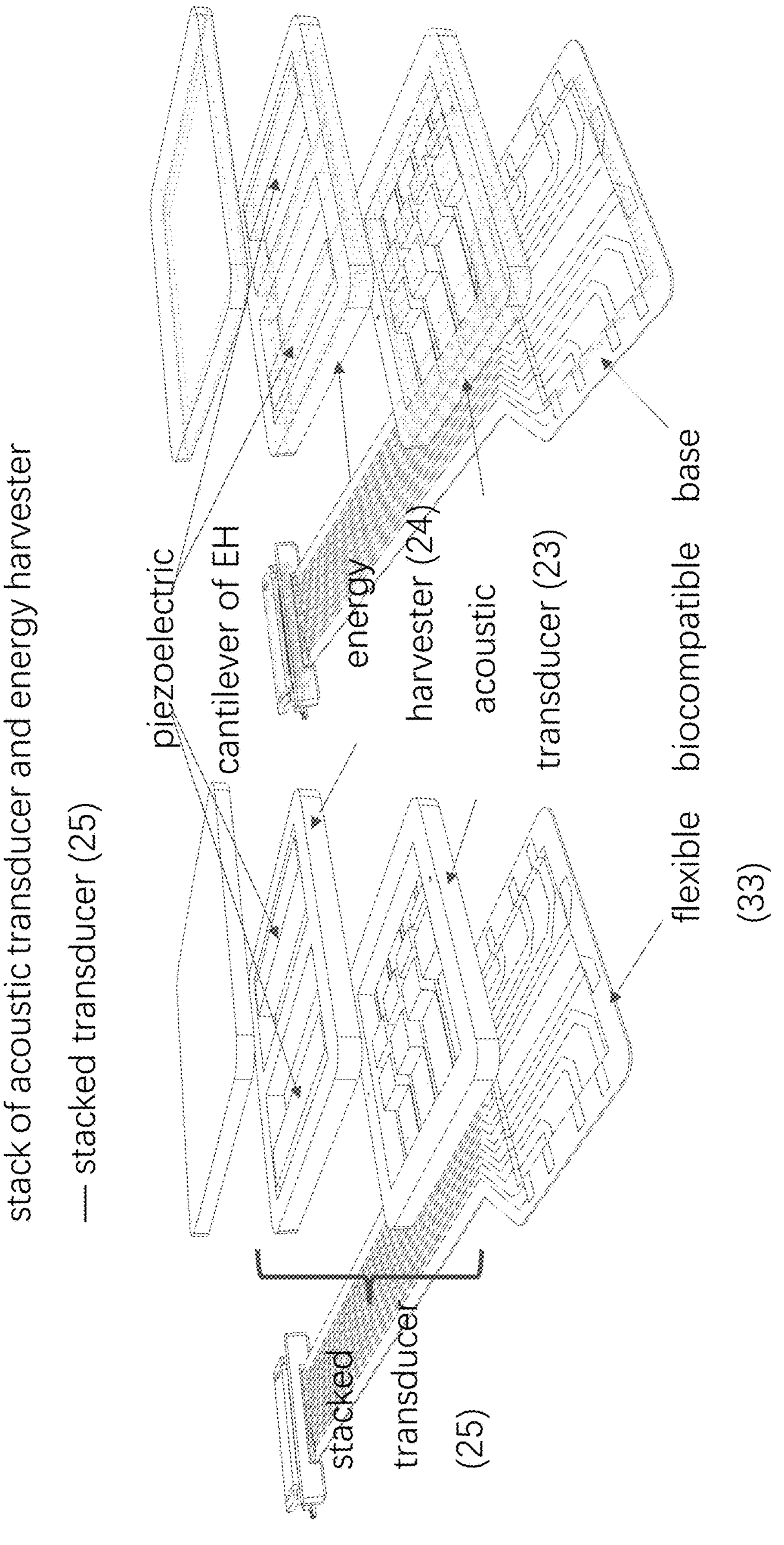
FIG. 5 depicts 3D view of stacked transducer and the substrate to be mounted according to the invention.

Integration:

For the effective implantation and long operation time of FICI units with minimum space requirement, effective integration and connection of the parts is crucial. For this purpose, energy harvesting and sound detector chips will be 3D integrated to form compact transducer stack (FIG. 5). This stack is hermetically packaged (may also be vacuum packaged) and interconnected with the power and signal conditioning CMOS interface circuits via flexible substrate. Due to the nature of invention, all the packaging of the FICI units are biocompatible for securing implantation.

Figure 3:
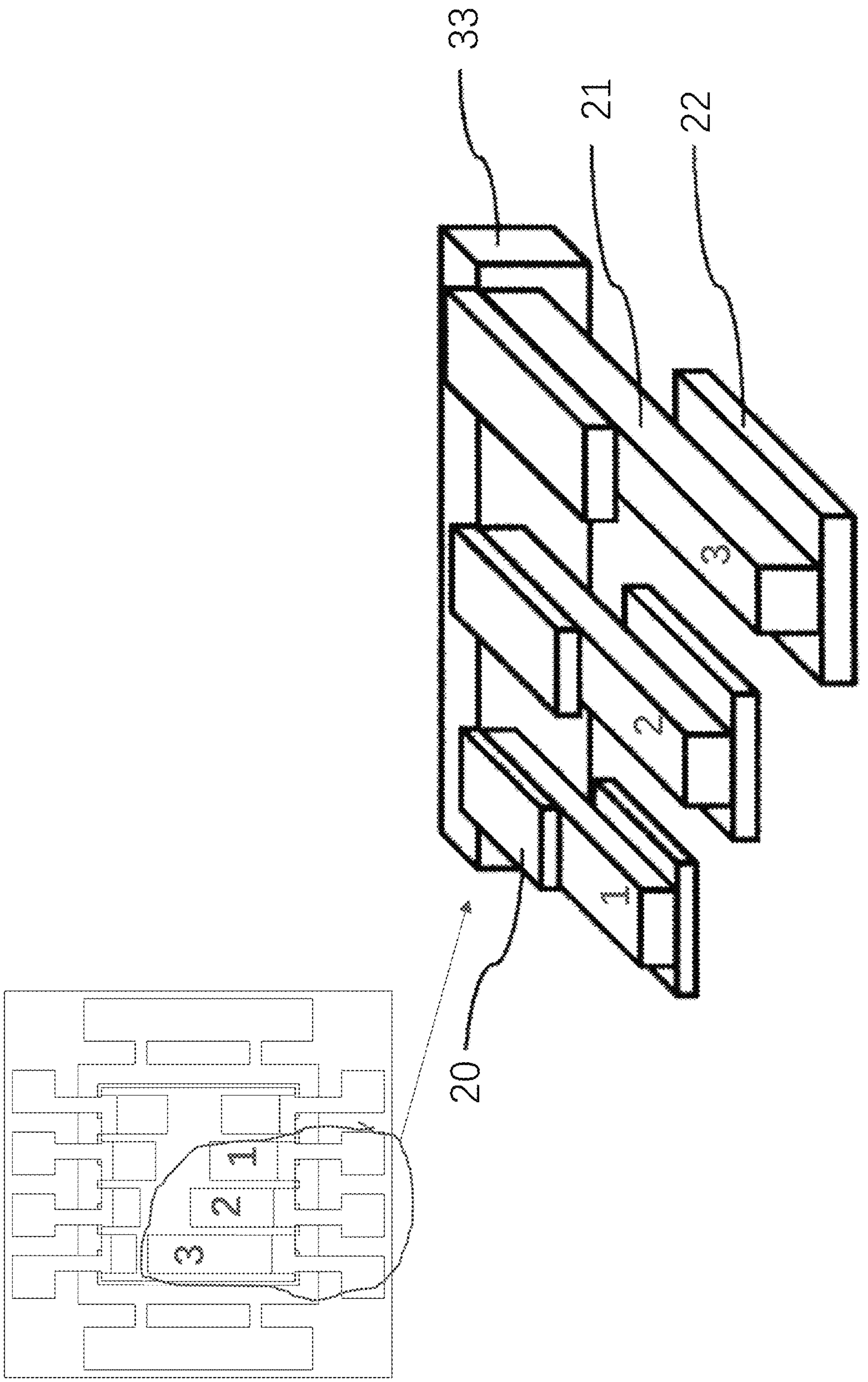
FIG. 3 is a partial view of a transducer according to the invention, depicting exemplary beams in detail.

As a summary: a harvesting and fully implantable cochlear implant system for providing electrical stimulation signals is proposed; where the system comprising:

Frequency selective piezoelectric cantilevers which is for generating the signals for neural stimulation, An acoustic transducer, shown in FIG. 3, wherein comprising a plurality of cantilever beams (21) and a piezoelectric piece (20) bonded to each of the cantilever beams (21); wherein each of the plurality of cantilever beams (21) has a different predetermined natural frequency from each other corresponds to 200 Hz-10 kHz frequency band of the incoming acoustic waves, An autonomous interface electronics which contains passive and active circuits with two storage elements including a capacitor and a rechargeable battery and wherein manages the extracted energy and provides regulated supplies for stimulation electronics and configured to connect to acoustic transducer and to receive and amplify the signals of the plurality of cantilever beams (21); and process circuits to stimulate the corresponding auditory nerves trough cochlear electrodes, Power conditioning IC (interface circuit) which is an autonomous self-adaptive system to extract acoustic energy via piezoelectric energy harvester for supplying power to neural stimulation electronics, An energy harvesting system wherein comprising piezoelectric cantilever to extract incoming acoustic energy available on auditory system, Wireless power transmission interface circuit which is for having a back-up and a supporting source to the energy harvester, The rechargeable battery implanted under the skin is recharged by an acoustic energy harvesting system At least one RF coil which is used as a wireless transfer for patient fitting and recharging the battery via attachable external coil as a back-up/support for the energy harvesting system.

OTHER ASPECTS OF THE INVENTION

The system, shown in FIG. 3, wherein each of the plurality of the cantilever beams (21) comprises one free end and one fixed end; the piezoelectric piece (20) is positioned on the fixed end; each of the plurality of cantilever beams (21) is capable of converting incoming acoustic waves to voltage outputs through the piezoelectric piece (20).

The system wherein energy harvesting system configured to charge rechargeable battery wherein comprises an interface circuit configured to connect to MEMS-fabricated piezoelectric harvester to extracted energy from said piezoelectric and manage the energy to provide regulated power supply; energy harvesting system extracts vibration energy available on middle ear auditory system.

The cochlear implant wherein further comprises: at least one flexible biocompatible base where said transducer, interface electronics and cochlear electrode are built upon. Said transducer attached on the said flexible biocompatible base is placed onto a vibrating element of an auditory system that vibrates under the influence of the incoming acoustic waves. Said flexible biocompatible base is patterned with a suitable serpentine electrode using a conductive metal for signal transfer between the transducers, interface electronics and the cochlear electrode.

The cochlear implant, shown in the FIGS., wherein each of the plurality of the cantilever beams (21) are designed to predetermine the natural frequency; wherein low frequency cantilever beam (21) incorporates a tip mass (22) on the free end and high frequency cantilever beams (21) are free of tip mass (22). Wherein each tip mass can comprise a rectangular structure with different length.

The cochlear implant wherein the number of the cantilever beams (21) can vary between 1 and 30 or as much as transducer stays at volume and mass limitation.

The cochlear implant wherein the transducer and energy harvester further comprise a biocompatible, hermetic coating and biocompatible covering of all system.

Figure 7A:
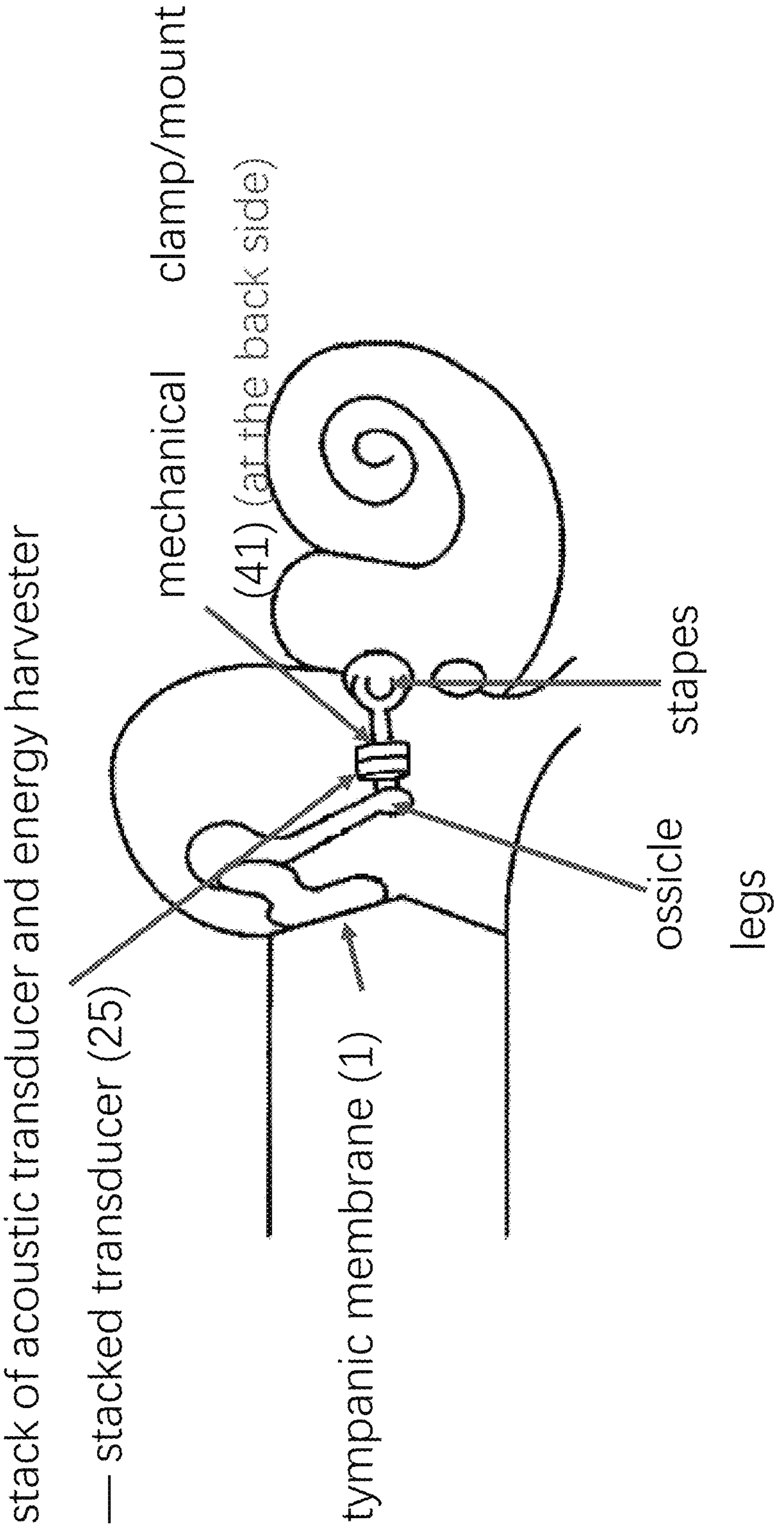
FIG. 7*a* is a schematic view of stacked transducer and harvester installed on stapes and the ossicles leg and shows it FIG. 7*b* installed on the incus.
Figure 7B:
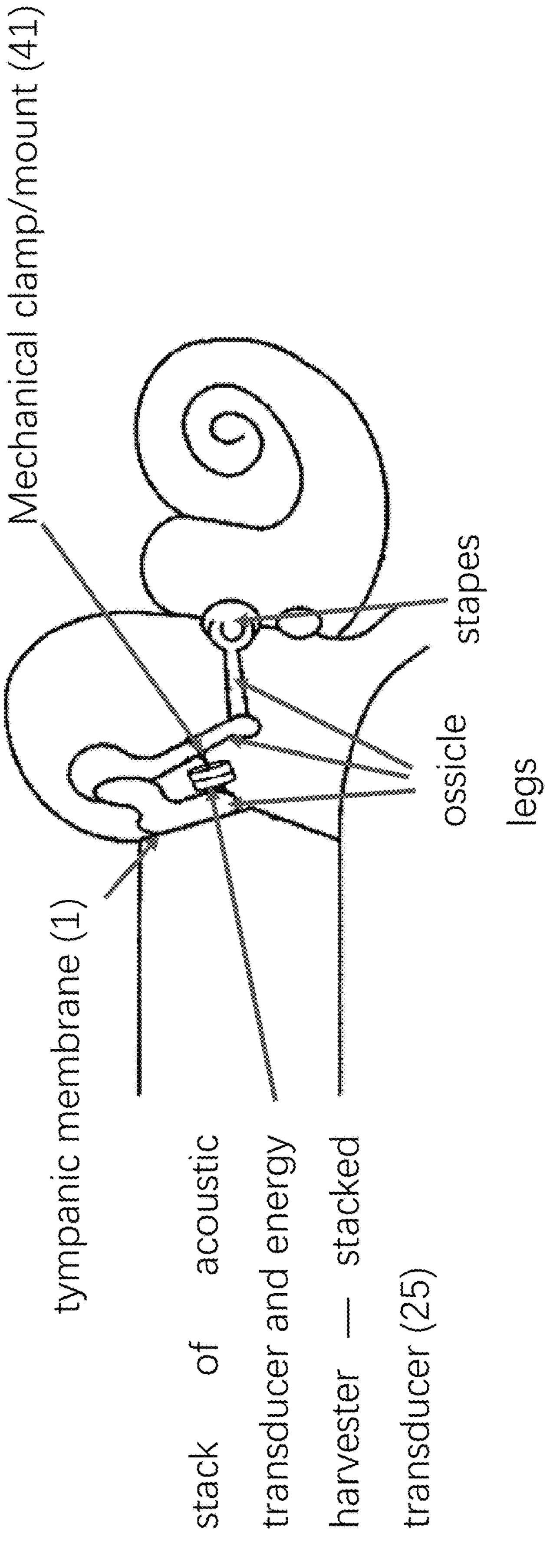

The cochlear implant wherein transducers are implanted into middle ear; preferably clamped between one of ossicle legs and umbo or one of ossicle legs and stapes and any of them that transfer vibration; referring to FIG. 7*a* and FIG. 7*b*.

The cochlear implant wherein further comprises wireless data transfer including implanted RF coil and connected electronics for fitting of the system and even power transfer to the battery.

Transducers are clamped between the umbo and ossicular chain (4) to sense the frequency of the vibrations of the incoming sound pressure waves.

Wireless data transfer including implanted RF coil and connected electronics for fitting of the system and even power transfer to the battery.

The piezoelectric piece (20) is positioned on the fixed end.

Each tip mass can comprise a rectangular structure with different length.

Energy harvesting system extracts vibration energy available on middle ear auditory system.

The system are implemented in middle and inner ear.

A rechargeable battery and the interface electronics associated with a coil are implanted under the skin.

The stack of acoustic transducer and energy harvester are mounted on one of the ossicles on the ossicular chain (2) or the tympanic membrane (1) to sense incoming sound and extract acoustic energy.

Transducers are all coated with a biocompatible material.

An energy harvesting system wherein comprising a wireless power transfer unit which is included in the package for recharging the battery, whenever the performance of energy harvester cannot cover the consumption of FICI package.

An RF coil placed next to the battery under the skin and external RF coil aligned to the implanted one is utilized not only to charge the battery when harvested energy is not sufficient but also for data transfer for patient fitting and diagnosis.

What is claimed is:

1. An energy-harvesting, fully implantable cochlear implant system for providing electrical stimulation signals, comprising:

an acoustic transducer including frequency-selective piezoelectric cantilevers configured to generate electrical signals for neural stimulation, the acoustic transducer comprising a plurality of cantilever beams and a piezoelectric piece bonded to each of the cantilever beams; wherein each of the plurality of cantilever beams has a different predetermined natural frequency corresponding to a 200 Hz-10 KHz frequency band of the incoming acoustic waves, an autonomous interface electronics that comprises passive and active circuits with two storage elements including a capacitor and a rechargeable battery and that manages the extracted energy and provides regulated supplies for stimulation electronics and is configured to connect to the acoustic transducer and to receive and amplify the signals of the plurality of cantilever beams; and process circuits to stimulate auditory nerves through cochlear electrodes, an energy-harvesting system comprising a piezoelectric cantilever configured to extract incoming acoustic energy available in the auditory system, a power-conditioning interface circuit configured to extract energy from the energy-harvesting system and to supply regulated power to the autonomous interface electronics, a wireless power transmission interface circuit configured to provide a back-up and supporting energy source to the energy-harvesting system, the rechargeable battery configured to be implanted under the skin and recharged by the energy-harvesting system, at least one radio-frequency (RF) coil usable for wireless transfer, patient fitting, and recharging the rechargeable battery via an external radio-frequency coil alignable with an implanted radio-frequency coil; and wherein each of the plurality of cantilever beams is designed to have a predetermined natural frequency; wherein a low-frequency cantilever beam incorporates a tip mass on the free end and high-frequency cantilever beams are free of the tip mass.

2. The system according to claim 1, wherein each of the plurality of cantilever beams comprises one free end and one fixed end and each of the plurality of cantilever beams is capable of converting incoming acoustic waves to voltage outputs through the piezoelectric piece.

3. The system according to claim 2, wherein the piezoelectric piece is positioned on the fixed end.

4. The system according to claim 1, wherein the power-conditioning interface circuit is configured to connect to a micro-electro-mechanical systems (MEMS)-fabricated piezoelectric harvester of the energy-harvesting system, to extract energy and manage the energy to provide a regulated power supply.

5. The system according to claim 4, wherein the energy-harvesting system extracts vibration energy available in the middle ear auditory system.

6. The system according to claim 1, further comprising at least one flexible biocompatible base on which the acoustic transducer, the autonomous interface electronics and a cochlear electrode are built; the flexible biocompatible base being configured to be placed onto a vibrating element of an auditory system that vibrates under the influence of the incoming acoustic waves.

7. The system according to claim 6, wherein the flexible biocompatible base is patterned with a serpentine electrode using a conductive metal for signal transfer between the acoustic transducer, the autonomous interface electronics, and the cochlear electrode.

8. The system according to claim 6, wherein the number of the cantilever beams of the acoustic transducer varies between 2 and 30.

9. The system according to claim 1, wherein the acoustic transducer and the energy harvesting system further comprise a biocompatible and hermetic coating and a biocompatible covering of the system.

10. The system according to claim 1, wherein the acoustic transducer and the energy-harvesting system are configured to be implanted into the middle ear.

11. The system according to claim 1, wherein the acoustic transducer is configured to be clamped between an ossicle leg and the umbo, or an ossicle leg and the stapes.

12. The system according to claim 1, wherein the acoustic transducer is configured to be clamped between the umbo and the ossicular chain to sense the frequency of the vibrations of the incoming sound pressure waves.

13. The system according to claim 1, further comprising wireless data transfer using the implanted radio-frequency (RF) coil and connected electronics for fitting of the system and for wireless power transfer to the rechargeable battery.

14. The system according to claim 1, wherein each tip mass comprises a rectangular structure with different length.

15. The system according to claim 1, wherein the system is configured to be implemented in the middle and the inner ear.

16. The system according to claim 1, wherein the rechargeable battery and the autonomous interface electronics associated with the implanted radio-frequency (RF) coil.

17. The system according to claim 1, wherein a stack of the acoustic transducer and the energy-harvesting system is configured to be mounted on one of the ossicles of the ossicular chain or the tympanic membrane to sense incoming sound and extract acoustic energy.

18. The system according to claim 1, wherein the acoustic transducer and the energy-harvesting system are each coated with a biocompatible material.

19. The system according to claim 1, further comprising a wireless power transfer unit included in the system for recharging the rechargeable battery, whenever the performance of the energy harvesting system cannot cover the consumption of the system.

20. The system according to claim 1, wherein a radio-frequency (RF) coil is positioned next to the rechargeable battery configured to be implanted under the skin, and an external radio-frequency (RF) coil is alignable with the radio-frequency (RF) coil to charge the rechargeable battery when harvested energy is not sufficient and to provide wireless data transfer for patient fitting and diagnosis.

* * * * *